US012752059B2

(12) United States Patent
Lebau et al.

(10) Patent No.: US 12,752,059 B2
(45) Date of Patent: Oct. 6, 2026

(54) INJECTION DEVICE AND A REUSABLE PART THEREFOR

(71) Applicant: Boehringer Ingelheim International GmbH, Ingelheim am Rhein (DE)

(72) Inventors: Olaf Lebau, Ingelheim am Rhein (DE); Joerg Heisiep, Ingelheim am Rhein (DE); Andree Jung, Ingelheim am Rhein (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 863 days.

(21) Appl. No.: 17/802,047

(22) PCT Filed: Feb. 25, 2021

(86) PCT No.: PCT/EP2021/054624
§ 371 (c)(1),
(2) Date: Aug. 24, 2022

(87) PCT Pub. No.: WO2021/170690
PCT Pub. Date: Sep. 2, 2021

(65) Prior Publication Data

US 2023/0131522 A1 Apr. 27, 2023

(30) Foreign Application Priority Data

Feb. 25, 2020 (EP) ..................................... 20159319

(51) Int. Cl.
*A61M 5/315* (2006.01)
*A61M 5/20* (2006.01)
(Continued)

(52) U.S. Cl.
CPC .......... *A61M 5/31568* (2013.01); *A61M 5/20* (2013.01); *G01F 23/2925* (2013.01);
(Continued)

(58) Field of Classification Search
CPC .. A61M 2205/3306; A61M 2205/3592; A61M 5/31568
See application file for complete search history.

(56) References Cited

U.S. PATENT DOCUMENTS 9,017,293 B2 4/2015 Edhouse et al.
9,429,713 B2 8/2016 Thornton, Jr.
(Continued)

FOREIGN PATENT DOCUMENTS

WO WO-2018069022 A1 * 4/2018 ............. A61M 5/24
WO 2019/106014 A1 6/2019
WO 2019/121447 A1 6/2019

*Primary Examiner* — Emily L Schmidt
(74) *Attorney, Agent, or Firm* — Calderon Safran & Wright P.C.; David S. Safran

(57) ABSTRACT

An injection device, in particular an auto-injector, with a single-use part for dispensing an injection solution has a sensor for acquiring a signal, with which an indicator can be determined, which represents a state or a change in state in a process for dispensing the injection solution with the single-use part. Additionally, the injection device has a reusable part, which is held in a detachable manner by coupling to the single-use part and is coupled via a signal connection, wherein the single-use part has the sensor, and/or wherein the reusable part has a reporting system for detecting the single-use part.

25 Claims, 5 Drawing Sheets

(51) Int. Cl.
*G01F 23/292* (2006.01)
*G02B 6/43* (2006.01)

(52) U.S. Cl.
CPC ............... *G02B 6/43* (2013.01); *A61M 5/315* (2013.01); *A61M 2205/3306* (2013.01)

(56) References Cited

U.S. PATENT DOCUMENTS

| | | | | |
|---|---|---|---|---|
| 9,563,023 | B2 | 2/2017 | Thornton, Jr. | |
| 9,737,665 | B2 | 8/2017 | Heumann et al. | |
| 9,750,882 | B2 | 9/2017 | Blei et al. | |
| 10,258,743 | B2 | 4/2019 | Whalley et al. | |
| 10,569,019 | B2 | 2/2020 | Hirschel et al. | |
| 10,857,303 | B2 | 12/2020 | Arenas Latorre et al. | |
| 10,881,813 | B2 | 1/2021 | Sall et al. | |
| 10,894,127 | B2 | 1/2021 | Tschirren et al. | |
| 11,007,322 | B2 | 5/2021 | Schabbach et al. | |
| 11,197,963 | B2 | 12/2021 | Helmer et al. | |
| 11,395,882 | B2 | 7/2022 | Helmer | |
| 2017/0312455 | A1 | 11/2017 | Mirov et al. | |
| 2018/0064881 | A1* | 3/2018 | Whalley | A61M 5/16886 |
| 2018/0200451 | A1 | 7/2018 | Shekalim | |
| 2018/0236185 | A1 | 8/2018 | Sall et al. | |
| 2019/0105476 | A1* | 4/2019 | Turtz | A61B 5/0031 |
| 2019/0240411 | A1 | 8/2019 | Keller et al. | |
| 2019/0388619 | A1 | 12/2019 | Hammen et al. | |
| 2020/0368442 | A1 | 11/2020 | Helmer et al. | |
| 2022/0031956 | A1* | 2/2022 | Helmer | A61M 5/3129 |

* cited by examiner

INJECTION DEVICE AND A REUSABLE PART THEREFOR

BACKGROUND OF THE INVENTION

Field of the Invention

This invention relates to injection devices that are suitable for administering an injection solution into a human or animal body.

In terms of this invention, injection devices are preferably devices that have a syringe and an injection needle that is coupled in a fluidic manner to the syringe, also called a cannula, which can be inserted into the body, in particular into the tissue and/or vessels thereof, and by means of which the injection solution can be administered through the cannula into the body.

In terms of this invention, in general an at least essentially liquid substance that can be injected is defined as an injection solution. In terms of this invention, the term “injection solution” is preferably to be defined broadly and also covers suspensions and other liquid substances that are suitable for injection and, preferably, contain a pharmaceutically effective active ingredient.

This invention relates in particular to injection devices in the form of so-called auto-injectors. In terms of this invention, auto-injectors are preferably injection devices for injection of an injection solution into a human or animal body, which bring about the injection of the injection solution automatically or semi-automatically by means of an automatism. In particular, a trigger mechanism is provided that triggers the automatic injection when activated by having an auto-injector be placed on a body part, by actuating a trigger, or the like.

By triggering an auto-injector, the injection solution is dispensed fully- or semi-automatically and can thus be inserted fully- or semi-automatically into the body. In particular, both an insertion of an injection needle and a subsequent dispensing of the injection solution through the injection needle into the body can be carried out fully- or semi-automatically. Preferably, the auto-injector can be put ahead of time into a trigger-ready state or has to be moved in this state, so that the triggering can take place. This can be done by removing a mechanical safety device such as a protective cap or in another way.

Description of the Related Art

Examples of auto-injectors and possible designs of a trigger mechanism that make the described triggering possible are described in European Patent Application 2 745 866 B1 and corresponding U.S. Pat. No. 10,894,127 B2, and European Patent Application 3 590 568 A1 and corresponding U.S. Pat. No. 10,569,019 B2.

In addition, this invention preferably relates to injection devices that have a single-use part for dispensing the injection solution or form the latter. In terms of this invention, a single-use part, also called a disposable part, is preferably a system that is designed for only one-time, non-permanent use or cannot be filled up without use of force and/or cannot be used multiple times.

The single-use part is preferably an auto-injector. In particular, in terms of this invention, the single-use part is an auto-injector that is designed for one-time use or as a disposable part. In particular, the auto-injector contains a syringe that cannot be filled up.

In addition, this invention relates to those injection devices in which a sensor for acquiring a signal is provided, with which an indicator can be determined that represents a state of the single-use part that is associated with the injection and/or a change in state of the single-use part in a process for dispensing the injection solution with the single-use part.

The sensor is preferably designed and/or arranged for direct or indirect acquisition of a fill level of the injection solution.

In terms of this invention, preferably a system that directly acquires the signal or is designed to do so is referred to as a sensor. In particular, in terms of this invention, the sensor is (only) one or more electrically merely passive system(s), in particular formed by one or more electrodes, coil windings, one or more lighting outlets and/or inlets, Hall probes, and/or other passive electrical components for acquiring the signal.

International Patent Application Publication WO 2017/050781 A1 and corresponding U.S. Pat. No. 11,197,963 B2, relate to a supplementary device in the form of an over-housing, into which an auto-injector with a dispensing device can be inserted and which has a capacitive sensor. The sensor has opposite plate electrodes, between which the dispensing device is arranged in the form of a syringe, which forms a part of a dielectric layer of the capacitive sensor, so that the dispensing of the contents of the dispensing device can be detected. As an alternative, a Hall sensor is described, with which magnetic fields of the moving parts of the dispensing device can be detected.

The supplementary device according to the state of the art must encompass the housing of the auto-injector, so that the sensor of the supplementary device can be influenced by the dispensing device. The resulting combination that consists of the supplementary device and the auto-injector, thus, is bulky and therefore has proven to be impractical. Moreover, the user has to exercise special care when arranging the supplementary device around the auto-injector in order to ensure the correct position of the housing and auto-injector with respect to one another and consequently to avoid measuring errors. The long distance between the sensor and the dispensing device based on this design creates greater susceptibility to interference due to possible introduction of disturbances such as noise. Finally, the sensor in the supplementary device may be subject to wear and tear when it has to be pushed along a short distance from the auto-injector in order to be able to influence the dispensing device in its position of use.

SUMMARY OF THE INVENTION

An object of this invention is therefore to indicate a solution in which a state or a change in state of an injection device can be detected, wherein the injection device is more compact and/or the detection is more reliable.

This object is achieved by an injection device according to claim 1 or a reusable part for this purpose according to claim 15. Advantageous further developments are the subject matter of the dependent claims.

According to a first aspect of this invention, the injection device has a multi-use reusable part in addition to the single-use part.

In terms of this invention, a reusable part preferably can be used multiple times in such a way that it can be coupled in succession to multiple, different single-use parts and in each case can serve its function, in particular can receive and/or evaluate the signal from the respective single-use part.

The reusable part has electronics. In terms of this invention, electronics are preferably a component that has an electric circuit, an (off-grid) power supply—in particular a battery, a storage battery, or a condenser—a processor, a storage device, and/or an output system for issuing an output, in particular a result of the evaluation of the signal that preferably originates from the single-use part or the sensor thereof.

Alternatively, or additionally, the reusable part can have one or more sensors. In particular, the reusable part can have one or more sensors for direct or indirect acquisition of the state or the change in state of the injection device, for supporting the acquisition of the state or the change in state of the injection device by the sensor of the single-use part, for verification of the acquisition of the state or the change in state of the injection device by the sensor of the single-use part, and/or for a plausibility check of the acquisition of the state or the change in state of the injection device by the sensor of the single-use part.

The single-use part and the reusable part can be coupled to one another in such a way that the single-use part and the reusable part are held to one another in a detachable manner, and a signal connection is produced between the single-use part and the reusable part. The signal can be transferred from the single-use part to the reusable part via the signal connection. By means of the signal, the indicator that represents the state that is associated with the injection and/or the change in state of the single-use part in the process of dispensing the injection solution with the single-use part can be determined.

The single-use part and the reusable part are preferably produced separately from one another or can be separated from one another. The single-use part can preferably also be used separately from the reusable part or without the reusable part, in particular as an auto-injector. The sensor is, however, preferably inoperable without the reusable part.

In terms of this invention, a state of the single-use part that is associated with the injection is preferably a variable property that relates directly to the dispensing of the injection solution, in particular usability for injection, or a parameter or a piece of information that corresponds in this respect via the dispensed or dispensable volume of the injection solution.

In terms of this invention, a change in state of the single-use part in the process for dispensing the injection solution is preferably a property of the single-use part that changes during the injection process, which property is characteristic of an injection process, for example by a movement of the piston or another part due to the continuous injection or a change or change in rate of the dispensed or dispensable volume of the injection solution or a parameter that corresponds thereto.

Especially preferably, the indicator represents or is thus a piece of information regarding the ability to dispense the injection solution and/or regarding the course of the dispensing of the injection solution.

In an advantageous way, it is provided that the signal, with which the indicator can be determined, or which forms the indicator, can be transferred via the coupling between the single-use part and the reusable part. In particular, it is provided that the signal is generated in the single-use part or with the single-use part and is transferred to the reusable part, whereupon the reusable part can acquire and/or process the signal with the electronics, so that preferably the indicator can be formed and even more preferably can be output.

In this aspect, the invention offers the advantage that the potentially valuable electronics of the reusable part can be used multiple times, while the single-use part is set up to generate the signal in a reliable way.

Alternatively, or additionally, it is not necessary and preferably not provided that the reusable part encompasses the single-use part in the area of the components that are instrumental for the injection in order to generate a signal with a sensor that is provided in the reusable part. In particular, the reusable part is designed as an extension of the single-use part. This allows for an extremely compact structural form.

The signal generation by the single-use part also has the advantage that a sensor that is necessary for this purpose is or can be arranged in the single-use part in immediate proximity to components involved in the dispensing of the injection solution, which improves the quality, in particular the signal-to-noise ratio, of the signal and thus, in the case of its evaluation, also the reliability of the indicator or the output.

According to another aspect of this invention, which can be realized independently, the single-use part has a cylinder for taking up the injection solution and a piston that can move in the cylinder for dispensing the injection solution.

In terms of this invention, a cylinder is preferably a part that forms a hollow cylinder, wherein injection solution can be taken up in the hollow cylinder. The cylinder preferably has an outlet through which the injection solution can be dispensed or is dispensed by moving the piston in the direction of the outlet. In terms of this invention, a piston is preferably a part that permanently rests snugly against the hollow cylinder inside wall that is mounted to move in the hollow cylinder, so that its movement changes, in particular reduces, the volume of the hollow cylinder that is between the piston and an outlet of the cylinder.

The combination of the cylinder with the piston is preferably a cylinder-piston unit, in particular a syringe. Accordingly, an injection needle (cannula) can be connected or is connectable to the outlet of the cylinder. Also, a discharge of the injection solution through the injection needle can be achieved by moving the piston in the cylinder.

The sensor is preferably arranged securely, permanently, inseparably, and/or immovably on or relative to the cylinder.

As a result of the sensor being provided as part of the single-use part securely, permanently, inseparably, and/or immovably relative to the cylinder, and even more preferably being arranged squarely, directly, or in any case directly adjacent to the cylinder, a signal of good quality or with a low signal-to-noise ratio can be generated. As a result, the signal enables an especially reliable determination of the indicator.

Also, corresponding to the nature of the single-use part, it is preferably provided that the sensor or the part of the sensor that is integrated into the single-use part preferably securely or inseparably from the latter is disposed of with the single-use part after use. This offers the advantage that components that are subject to some wear and tear are exchanged when another single-use part is coupled to the reusable part.

The signal preferably corresponds to a position or movement of the piston that accompanies the dispensing of the injection solution and that can be detected by the sensor, another movement that accompanies the dispensing of the injection solution and that can be detected with the sensor, and/or to a volume or a change in volume of the injection solution that can be detected with the sensor. In particular, the signal has corresponding information/signal parts.

While the single-use part preferably has the sensor that is designed and arranged for acquiring the signal, the electronics for evaluating the signal and, even more preferably, also an interface, an emitter, a detector, or the like for acquiring the signal (exclusively) are integrated into the reusable part or are formed by the reusable part.

In turn, the reusable part can preferably be used multiple times, so that the electronics including some electronic components that are assigned to the sensor—such as an interface, an emitter, a detector, or the like—can be used multiple times.

The reusable part can be made especially compact, for example as a housing extension. The reusable part is preferably designed without- or without the necessity for-encompassing the single-use part and/or in such a way that the sensor is integrated into the single-use part to be able to be coupled to the single-use part.

Moreover, it is especially preferred that the reusable part only, in particular slightly, extends beyond the single-use part. The reusable part can thus represent a (at least essentially exclusive) housing extension of the single-use part. In particular, the reusable part forms a housing extension for the housing of the single-use part, wherein the diameter and/or peripheral surfaces of the single-use part and the reusable part in the area of a contact point between the single-use part and the reusable part deviates less than 30% or 20%, in particular less than 10% or 5%.

In this regard, the reusable part can have a circumferential wall, which aligns with a circumferential wall of the single-use part, when the single-use part and the reusable part are coupled. This preferably has the effect that even in the case of a reusable part that is coupled to the single-use part, the injection device—as a whole and in any case in the area of the transition from the single-use part to the reusable part—forms or enables an at least essentially continuous or interruption-free housing interface or silhouette.

Another aspect of this invention, which can also be realized independently, relates to an injection device with the single-use part and a multi-use reusable part that has electronics, wherein the single-use part and the reusable part can be coupled to one another, and the reusable part has a reporting system for detecting the single-use part.

In terms of this invention, a reporting system is preferably a system for detecting a presence of a single-use part that is coupled or can be coupled to the reusable part and/or for reading out information that is stored or can be stored on or at the single-use part, preferably identification, in particular an indicator that clearly identifies an individual or a group such as a batch or a type of single-use parts.

In an aspect that can also be realized independently, this invention accordingly relates to a system with one or more single-use parts, which in each case can have such information, and at least one reusable part with a reporting device for reading out this information in the event of, by, or after coupling with the respective single-use part.

The single-use part can have or can store the information for example, in the form of an RFID emitter, barcodes including QR codes and the like, and/or on an electronic storage device, in particular a flash storage device.

The reporting device can be a reader for the information, preferably a wireless reader, RFID reader, barcode reader, or the like.

Alternatively, or additionally, the reporting device can be coupled with a (hard-wired) interface to the single-use part and/or can be coupled to an interface for transferring the signal, and via this interface, the information can be read out from the single-use part or can be designed to do so.

Alternatively, or additionally, the reporting device can detect and/or report the presence of a single-use part, wherein an identification of the single-use part does not necessarily have to take place. For this purpose, the reporting device can have or can form a position sensor and/or approach sensor, a switch, an optical sensor, a Hall sensor, or the like, with which an approach and/or coupling of the reusable part to a single-use part can be detected.

Alternatively, or additionally, the reporting device can detect a start-up, a beginning of an application, a coupling of the single-use part to the reusable part, preferably by detection of a relative movement of the single-use part to the reusable part and/or by detection of a contact pressure of the single-use part on the reusable part or vice versa. For this purpose, a movement in an axial direction can be possible or detectable in the single-use part. In particular, the reusable part can move relative to the single-use part or the reusable part together or coupled to a part of the single-use part in the axial direction, and/or such an axial movement or a pressure, in order to bring it about, can be detected by the reporting device. A sensor for detecting the coupling, the relative movement, axial movement, and/or the pressure can be provided in the reusable part, alternatively or additionally, however, also in the single-use part.

The reusable part, in particular the reporting device, can be designed for detecting a use of the injection device, in particular for detecting a triggering or a start of injection and optionally for signaling or producing an output that represents the triggering or the start of injection or is based thereon. The detection of the triggering or the start of injection can be used or combined with the signal, with which the indicator can be determined. In particular, the signal is processed together with or with allowance for the detection of the triggering or the start of injection, or the indicator is determined in this respect.

The reporting device can be designed for switching the reusable part on and off. In particular, the reusable part is designed to switch the reusable part on when coupling with a single-use part is detected or to switch the reporting device off when the loss of coupling with the single-use part is detected. In this regard, the terms "switching on" or "switching off" preferably cover the wakeup or activation from an energy-efficient mode (standby mode).

Another aspect of this invention, which can also be realized independently, relates to a reusable part for an injection device according to one of the preceding aspects. The reusable part can be used multiple times and has electronics. Also, the reusable part can be coupled to the single-use part that has the sensor, so that the single-use part and the reusable part are held to one another in a detachable manner, and the signal connection between the single-use part and the reusable part is produced, via which the signal can be transferred from the single-use part to the reusable part and can be evaluated by the electronics of the single-use part. Alternatively, or additionally, the reusable part has a reporting system for detecting the single-use part of the injection device.

Additional advantages, aspects and properties of the present invention will become apparent from the following description of the preferred embodiments with reference to the accompanying drawings.

DETAILED DESCRIPTION OF THE INVENTION

Below, reference numbers that are the same or that correspond to one another are used for the same or similar parts, wherein parts with the same and similar reference numbers can have the same or similar properties and advantages even if a description is not repeated.

Figure 1:
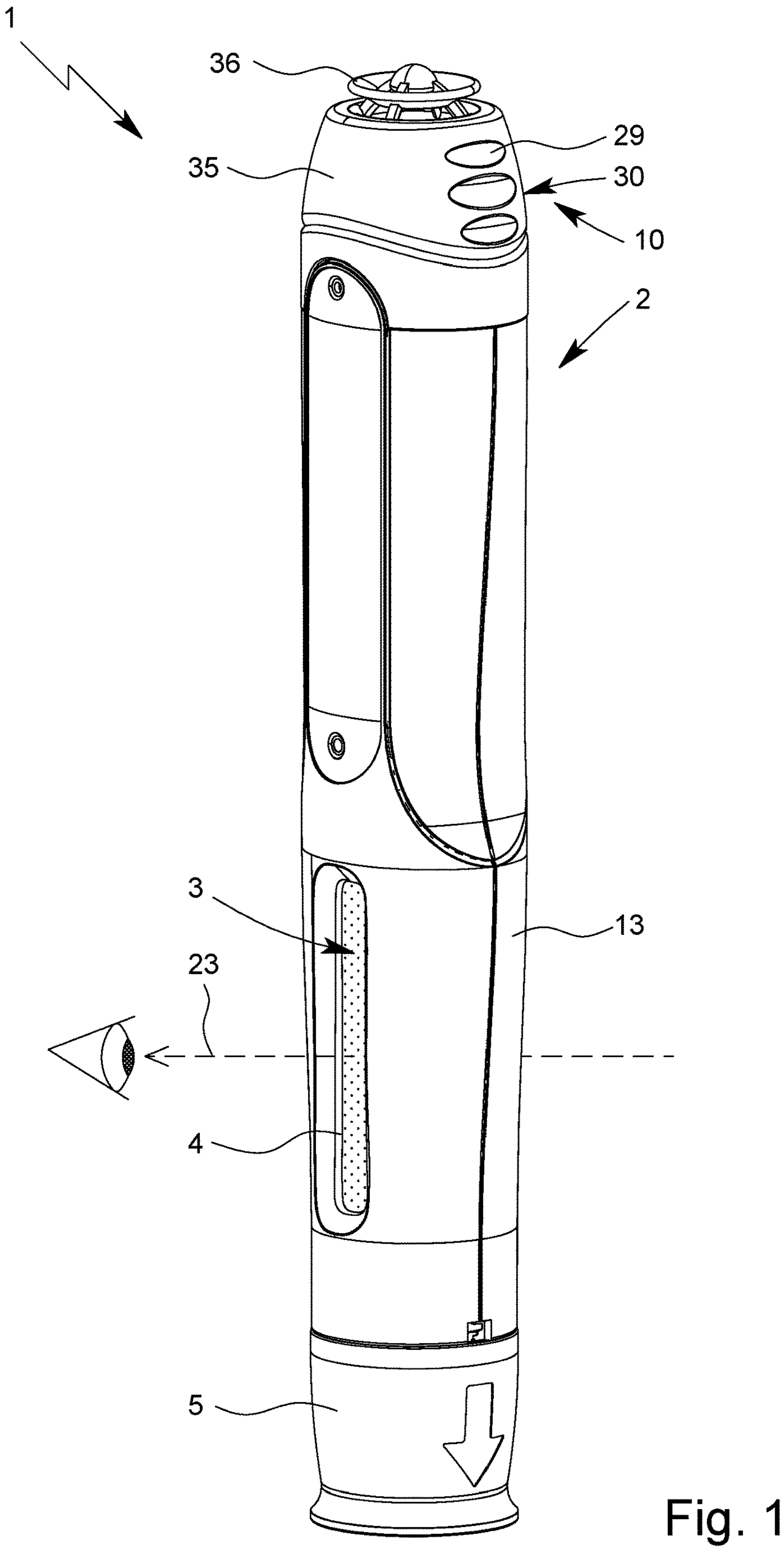
FIG. 1 is a schematic view of an injection device according to the present invention.

In FIG. 1, an injection device 1 according to the present invention is depicted schematically. The injection device 1 preferably has a single-use part 2 for dispensing an injection solution 3. In FIG. 1, the injection solution 3 is indicated by dotting.

The injection device 1, and in particular the single-use part 2, preferably has a so-called auto-injector or forms the latter. With respect to the basic properties of auto-injectors, at this point, reference can be made to the explanations in the general description section and to the above-mentioned prior art relating to the known auto-injectors.

In the illustrative example, the single-use part has a window 4, through which the injection solution 3 can be seen. The window 4 is optional, so that the single-use part 2 or the injection device 1 can be produced even without such a window 4.

Moreover, the injection device 1 according to FIG. 1 has a protective cap 5, which closes the single-use part 2 and/or secures against accidental actuation or triggering. The protective cap 5 is not necessarily provided, however. A safety device against accidental triggering can also be provided and/or another closure can be provided.

Figure 2:
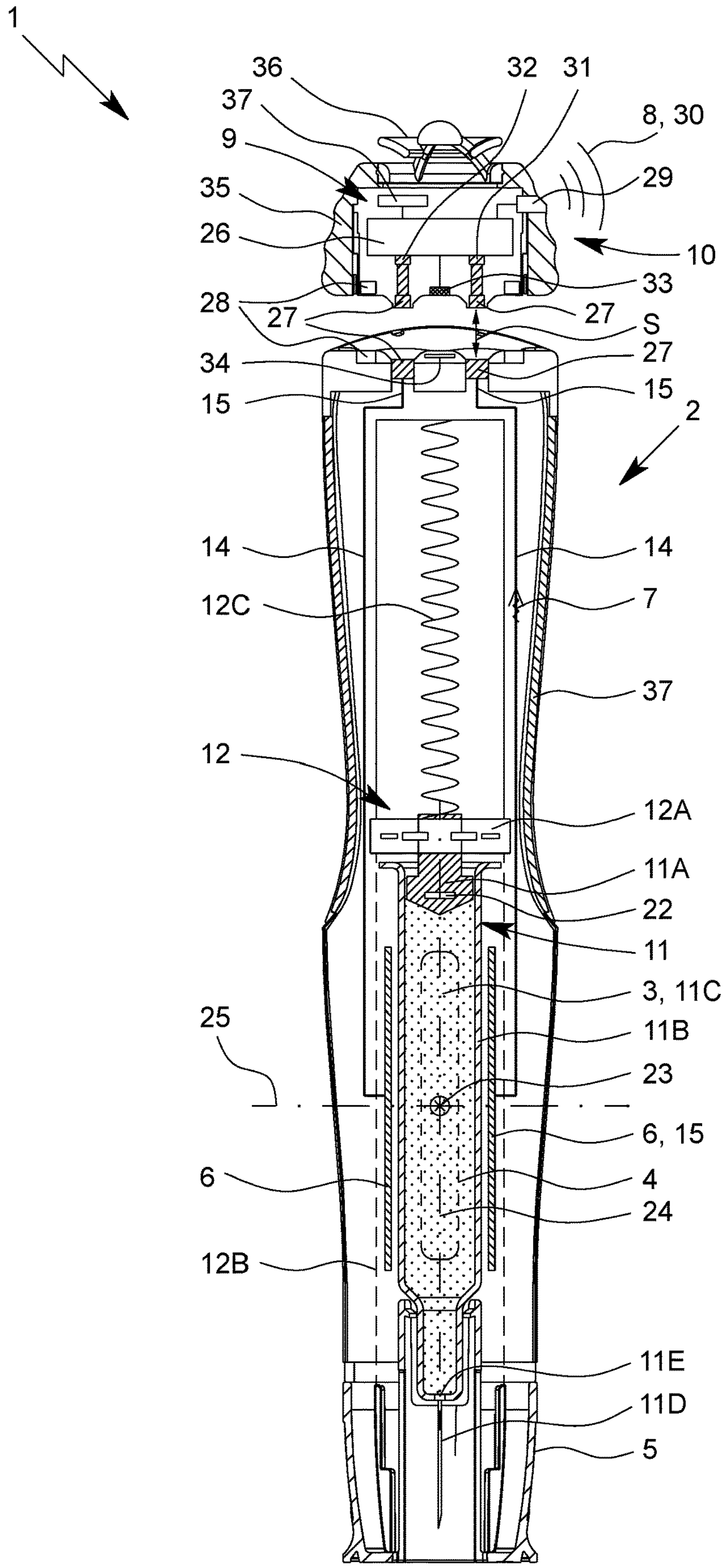
FIG. 2 is a schematic longitudinal section of the injection device according to the present invention.

In FIG. 2, a greatly simplified, schematic longitudinal section of the injection device 1 according to the present invention is depicted.

The injection device 1 according to the present invention has a sensor 6 for acquiring a signal 7, indicated with a zigzag line or an arrow in the illustrative example according to FIG. 1.

The signal 7 is preferably suitable for ensuring that an indicator 8 can be determined with the latter, wherein the indicator 8 represents a state or a change in state of the single-use part 2 in a process for dispensing the injection solution 3.

Accordingly, the signal 7 preferably has information that corresponds to the state or the change in state, so that the indicator 8 can be determined.

The state is in particular information on the fill level, the trigger-readiness, or quite generally the usability of the single-use part 2 for injection of the injection solution 3 and/or a value or parameter that corresponds thereto, such as, for example, a piston position, which corresponds to the residual volume of the injection solution 3 in the cylinder 11. The change in state is preferably information regarding the change of such a state.

In principle, the indicator 8 can be formed by the signal 7 or can be derived directly from the signal 7, for example by conversion. The determination of the indicator 8, however, preferably requires a processing of the signal 7, in particular (digital) signal processing or evaluation. In this regard, in particular a comparison with a reference or threshold value or other criterion can be carried out.

The injection device 1 preferably has a multi-use reusable part 10 that has electronics 9. The reusable part 10 is preferably a separate reusable module that can be separated from the single-use part 2.

The single-use part 2 and the reusable part 10 can be coupled to one another in such a way that the single-use part 2 and the reusable part 10 are held to one another in a detachable manner and, preferably simultaneously and/or by this coupling, a signal connection S can be produced or is produced between the single-use part 2 and the reusable part 10, via which the signal 7 can be transferred from the single-use part 2 to the reusable part 10.

The reusable part 10 preferably has a housing 35, in which the electronics 9 are accommodated. In the illustrative example, the housing 35 has a handle 36. The latter is optional, however, and is not necessary if a part of the housing 35 acts as a handle section.

Especially preferably, the housing 35 of the reusable part 10 represents a removable (axial) extension of a housing 13 of the single-use part 2. To this end, the housings 13, 35 in each case can have at least essentially cylindrical side walls, which have a radius that is at least essentially the same or similar and/or align with one another when the single-use part 2 is coupled to the reusable part 10, so that the reusable part 10 only extends the single-use part 2, without the single-use part 2 having to be inserted into the reusable part 10.

Since components for automatic injection of the single-use part 2 can be produced preferably in principle like auto-injectors known from the state of the art, more detailed discussion below will focus only on parts thereof that are potentially relevant for this invention.

The single-use part 2 preferably has a cylinder 11 for taking up the injection solution 3 and a piston 11A that can be moved in the cylinder 11 for dispensing the injection solution 3.

The piston 11A is also called a plunger, so that the terms "piston 11A" and "plunger" are interchangeable in terms of this invention. The piston 11A can have a drive 12C or a part thereof or be formed herewith.

The piston 11A is preferably suitable for pressurizing the injection solution 3 in a cylindrical inside space 11C formed by a cylinder wall 11B of the cylinder 11, so that the injection solution 3 is dispensed, in particular by an injection needle 11D, which can be coupled accordingly to an outlet 11E of the cylinder 11.

The sensor 6 is preferably arranged, in particular directly, permanently, and/or inseparably, at or on the cylinder 11—in particular at, on, and/or directly adjacent to an outer side of the cylinder wall 11B of the cylinder 11 that bounds a cylindrical inside space 11C for taking up the injection solution 3.

The sensor 6 is preferably designed, arranged, and/or is suitable for detecting a movement of the piston 11A that accompanies the dispensing of the injection solution 3 and/or (in another way) the dispensing of the injection solution 3. This is preferably done by forming and/or acquiring the signal 7, by information regarding the movement of the piston 11A that accompanies the dispensing of the injection solution 3 and/or information that represents (in another way) the dispensing of the injection solution 3 being converted into the signal 7 or being added to the signal 7.

As a result, the signal 7 can contain information that corresponds to the dispensing of the injection solution 3 or movement of the piston 11A. Thus, the signal 7 is suitable in that the indicator 8 can be determined from the latter.

Also, an injection mechanism 12 can be provided that is suitable for moving the piston 11A inside the cylinder 11 during activation, so that the injection solution 3 that is taken up and/or can be taken up in the cylindrical inside space 11C is pressurized and dispensed through an outlet 11E of the cylinder 11.

In principle, the injection device 1 can be operated manually, in particular by manual movement of the piston 11A. In the preferred case that the injection device 1 is an auto-injector, preferably a triggering system 12A that activates the injection mechanism 12 during triggering is provided.

In this regard, a triggering part 12B can be provided in order to actuate the triggering system 12A. The triggering part 12B can in principle be a button, switch, or the like. In the illustrative example, the triggering part 12B is formed by a mechanism that causes triggering of the triggering system 12A during positioning of the injection device 1 or the single-use part 2.

In addition, a drive 12C can be provided, in particular a tension element or having a tension element, such as a spring, which drives the piston 11A when the triggering system 12A is triggered.

Finally, in the illustrative example, the housing 13 of the single-use part 2 is indicated, which housing in this invention preferably accommodates at least the cylinder 11, the piston 11A, the sensor 6, and, preferably, the injection mechanism 12.

The housing 13 is made preferably elongated or pipe-like, as is known in principle from auto-injectors, in particular pencil-shaped auto-injectors, also called pens.

The sensor 6 is preferably designed for generating the signal 7, which as a result preferably contains information regarding a continuous injection with the single-use part 2, regarding a primary usefulness or uselessness of the single-use part 2 for executing an injection, regarding trigger-readiness of the single-use part 2, and/or regarding deficient trigger-readiness of the single-use part 2 for injection.

As schematically indicated in FIG. 2, the sensor 6 or the single-use part 2 can have at least one line 14 preferably along the cylinder 11 and/or routed through the housing 13, via which the signal 7 is routed or directed. The line 14 can be connected via a connection 15 to the reusable part 10 or to a connector 27 for producing the signal connection S with the reusable part 10.

In the illustrative example, two or more lines 14 are provided, wherein the signal 7 is routed at least over one of these lines 14.

In principle, at least two signal transmission lines 14 can also be provided, and/or the signal 7 can be transmitted via two or more lines 14, in particular differentially.

Quite especially preferably, at least two lines 14 that connect or couple the sensor 6 or one or various connections 15 of the sensor 6 are provided. The sensor 6 and in any case a part of the line(s) 14 is/are preferably produced by or in the single-use part 2 or arranged (securely, permanently/integrally/in one piece).

The line(s) 14 can be designed for conducting electric current or electrical signals 7. Alternatively or additionally, the latter, in particular when the sensor 6 is optical, are designed as optical wave guides, also called optical cable, optical fibre, light wave guide or fibre optical cable.

The line(s) 14, in particular in the form of one or more optical wave guides, can be integrated (securely or permanently) in an especially advantageous way into the housing 13 or a component of the single-use part 2.

In this regard, the line(s) 14 is/are preferably formed by a or with a light-conducting or transparent plastic, which is integrated into the housing 13 or into another component of the single-use part 2, preferably also otherwise formed from a plastic, or is formed with the latter. In this regard, the line(s) 14 can be formed by a light-conducting, in particular injection-molded, plastic.

For example, it is possible in an advantageous way to integrate light-conducting plastic as line 14 by means of an (in particular two-component) injection-molding method into the housing 13, preferably consisting of plastic, and/or other component of the single-use part 2 or to fasten it thereby.

The sensor(s) 6 is/are preferably designed for optical, acoustic, capacitive, inductive, and/or impedance-measurement-based acquisition of the signal 7.

In FIG. 2, a general, in particular capacitive, sensor 6 is indicated by way of example. In this regard, FIG. 3 shows a sectional schematic view of the cylinder 11 with the piston 11A and one or more capacitive sensor(s) 6.

Figure 3:
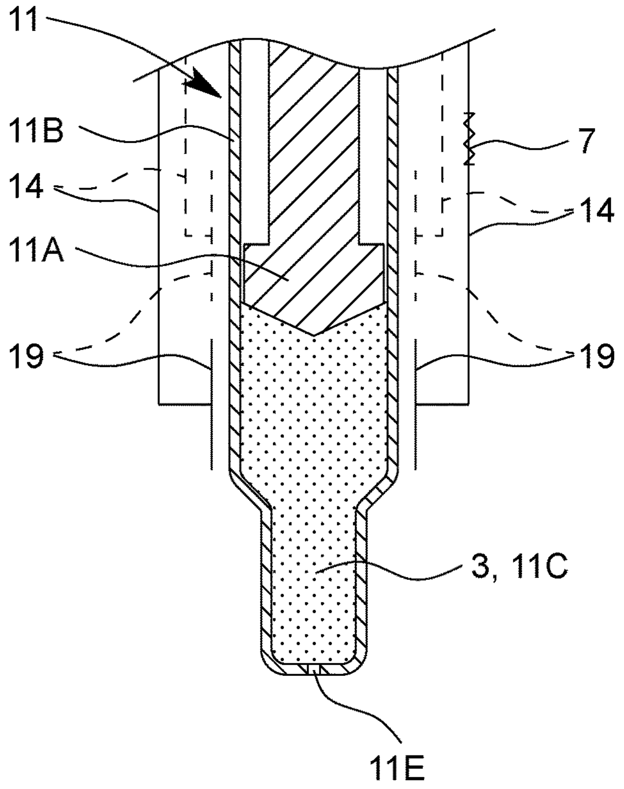
FIG. 3 is a sectional schematic view of the single-use part of the injection device according to the present invention with a capacitive sensor.

In the illustrative example according to FIG. 3, the sensor 6 is designed for capacitive acquisition of the signal 7. For this purpose, two or more electrodes 19 can be provided that form a capacitor (a condenser, in particular plate condenser), whose capacity value depends on the position of the piston or the fill level and/or the dispensing of the injection solution 3.

Accordingly, the signal 7 for this purpose can represent corresponding capacitive properties of the capacitive sensor 6.

In the illustrative example, the sensor 6 has electrodes 19 on different, opposite, sides of the cylinder 11, so that the electrical/dielectrical properties of the cylinder 11 between these electrodes 9 depend on the position of the piston 11A and/or on the fill level of the cylinder 11 with the injection solution 3. In this way, the capacity value of the capacitive sensor 6 that is formed with the electrodes 19 preferably corresponds to the fill level of the injection solution 3 in the cylinder 11 and/or a position of the piston 11A as a state or to a change of the latter as a change in state.

Optionally, multiple capacitive sensors 6 or a capacitive sensor 6 can be provided with multiple electrode pairs 19, as indicated in broken lines in FIG. 3, which are arranged distributed preferably along the cylinder 11 or the piston path during the injection process. In this way, accuracy can be improved.

Figure 4:
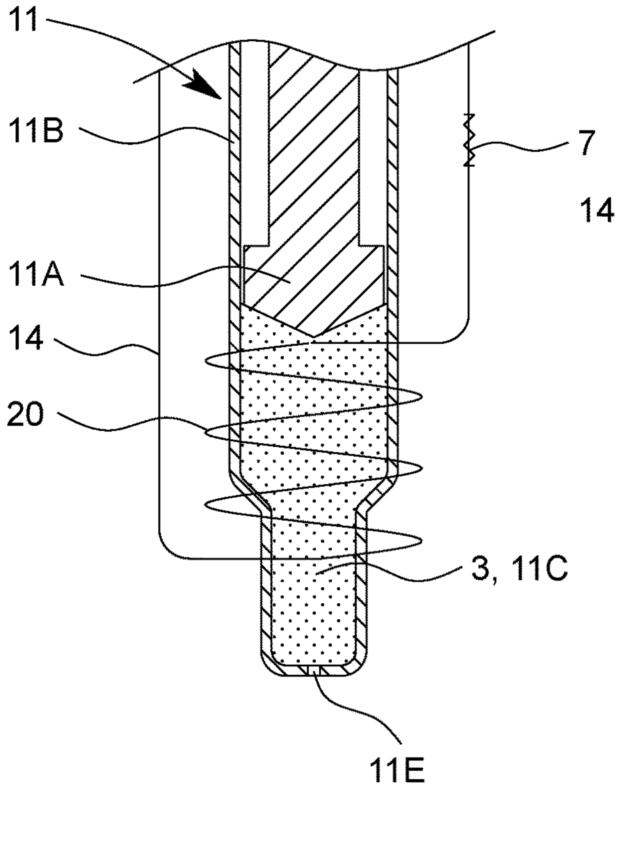
FIG. 4 is a sectional schematic view of the single-use part of the injection device according to the present invention with an inductive sensor.

In FIG. 4, an inductive sensor 6 is provided, in particular in the form of a—or having a—coil 20. This can be designed to bring about an inductive coupling with the injection solution 3 and/or the piston 11A, so that the electrical properties or parameters of the coil 20, in particular those that represent their electrical quality, depend on the position of the piston 11A or the fill level of the injection solution 3 in the cylinder 11. This makes it possible to acquire the signal 7, which is generated or varied in this regard preferably by the change in properties of the coil 20 and as a result is suitable for determining the indicator 8.

The piston 11A or a drive for the latter or part thereof can be formed from a ferromagnetic material, magnetizable material, or material that can be magnetically detected in another way or can have the latter. Alternatively, or additionally, the piston 11A or the drive for the latter or a part thereof can be formed from an electrically-conductive or semi-conductive material or can have the latter.

The sensor 6 is preferably designed to form the signal 7, based on this material and, preferably, the movement of the material in the course of the dispensing of the injection solution. The inductivity and/or quality of the inductive sensor 6 or the coil 20 can vary from the position of the piston 11A based on the material, in particular in such a way or so that the position of the piston 11A is in a direct connection with the inductivity and/or quality of the coil 20. The signal 7 preferably corresponds to this inductivity and/or quality of the coil 20 or represents the latter. Accordingly, the indicator 8 can be determined by evaluating the signal 7 based on the inductivity that varies with the change in position of the piston 11A and/or quality of the coil 20.

Alternatively, or additionally, the sensor 6 can be designed for impedance-based acquisition of the signal 7. For this purpose, one or more of the previously-described sensors 6, in particular an inductive and/or a capacitive sensor 6, can be used or combined in order to determine the signal 7 that depends on the fill level of the injection solution 3 and/or the position of the piston 11A based on the impedance property of the cylinder 11, the piston position, and/or the fill level of the injection solution 3.

In particular, a signal 7 can be acquired that enables to determine the fill level of the injection solution 3 or the position of the piston 11A in particular by damping (signal losses varying due to conversion of signal energy in heat, eddy-current losses or the like) and/or based on phase relationships to a reference or between current and voltage and/or of phase changes of the signal 7.

In the illustrative example, the coil 20 is arranged, in particular wound, around the cylinder 11. It is understood that this is effective, but not necessary, and alternatively or additionally, a coil 20 can also be provided adjacent to the cylinder 11.

When the coil 20 is arranged around the cylinder 11, the windings forming them cover preferably less than 50%, preferably less than 40% or 30%, in particular less than 20% or 10%, of the window 4.

If the sensor 6 is embodied as a coil 20 or is designed in another way for determining magnetic properties, the latter can detect in particular the magnetic permeability of the content that is located in the cylinder 11. This is further changed preferably by dispensing the injection solution 3 from the inside space 11C of the cylinder 11 and/or the movement of the piston 11A that corresponds thereto, so that the signal 7 can be picked up with the sensor 6 and can be evaluated, if necessary, with the reusable part 10.

Alternatively, or additionally to the coil 20, the sensor 6 can have a Hall probe or can be made in this way. A Hall probe is suitable for picking up static magnetic fields. For this purpose, the piston 11A can have a magnet 22, as indicated in FIG. 2, or can be formed by a magnet 22 or magnetic material. In this way, a signal 7 that corresponds to the position of the piston 11A can be generated by means of the Hall probe as a magnetic field sensor, from which signal in turn the indicator 8 can be determined.

The sensor 6 is optical in an especially preferred variant of the injection device 1 according to the present invention. The sensor 6 is thus preferably designed for optical acquisition of the signal 7. An example of this is shown in FIG. 5.

In this case, the signal 7 is preferably optical, and/or the line(s) 14 is/are optical lines 14. The signal 7 is correspondingly optical (light) and contains optical information, in particular by modulation of the light intensity, and/or wavelength, by which the indicator 8 can be determined, if necessary. This can be done in such a way that with the optical sensor 6, a fill level of the cylinder 11 or a change in fill level is optically detected or can be detected directly or indirectly via a position or movement of the piston 11A.

Figure 5:
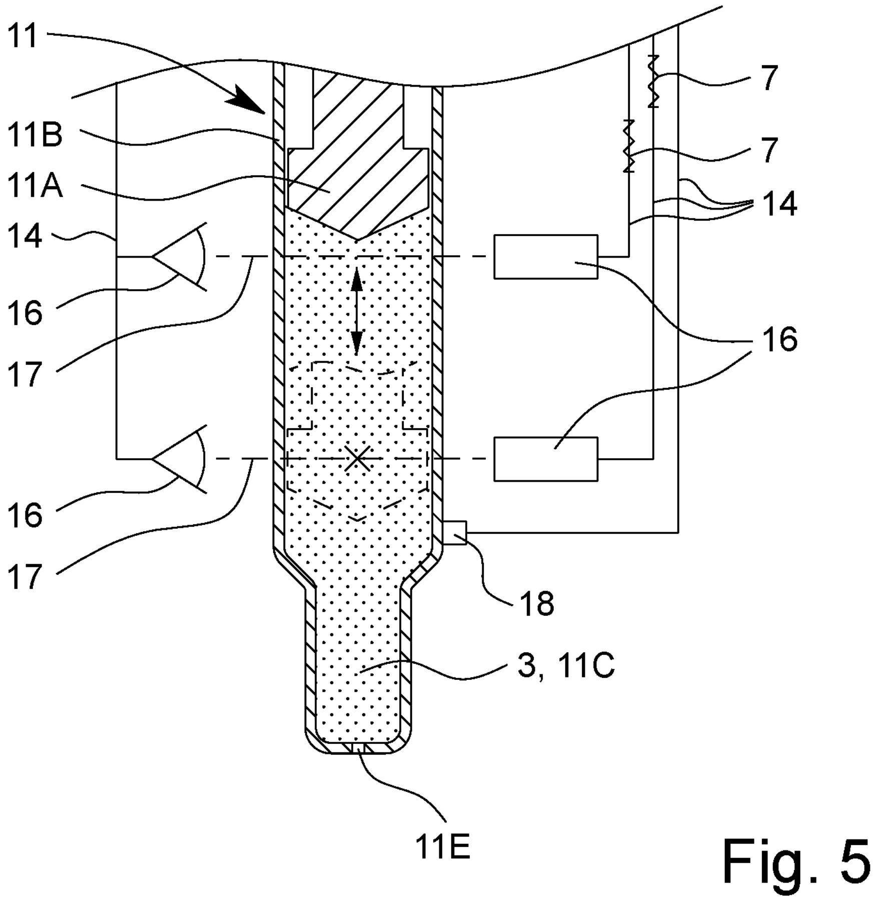
FIG. 5 is a sectional schematic view of the single-use part of the injection device according to the present invention with an optical sensor.

As shown in FIG. 5 by way of example, for this purpose, the sensor 6 can have or form one or more light gates 16, by which at least one position of the piston 11A can be determined. This can be done in such a way that at least one of the light gates 16 monitors an optical path 17 through the injection solution 3 and/or in principle optical transmission properties of the cylinder—in particular as a function of the position of the piston 11A.

In this embodiment, the line(s) 14 is/are preferably one or more optical (wave) guides or light wave guides, in particular glass fiber(s) or polymer optical fiber(s). In this way, an optical acquisition and transfer of the signal 7 can be carried out economically and reliably. In this regard, electrical components are preferably provided exclusively in the reusable part 10. The single-use part 2, however, is preferably free of electrical components, in any case for generating, transferring, and/or evaluating the signal 7. The line(s) 14 preferably connect(s) the sensor(s) 6 inside the single-use part 2. The optical sensor 6 is preferably formed by or with open ends of the lines 14 in the form of optical/light wave guides, by which one or more light gates 16 can be produced.

In FIG. 5, one or more optical paths 17, which (in each case) is/are monitored by a light gate 16, is/are drawn in as broken lines. With an interruption or release of the optical path 17/one of the optical paths 17, the optical sensor 6 can accordingly generate a signal 7 that corresponds thereto.

In this case, the signal 7 can be optical in nature, i.e., a light signal. In addition, it can be provided that as a function of a fill level of the injection solution 3 in the cylinder 11 or a position of the piston 11A, the signal 7 has light or not or is brighter or darker. In principle, multiple sensors 6 can be provided, which in each case are designed for generating a signal 7 or a part thereof.

As also indicated in FIG. 5, multiple light gates 16 can be provided at various positions, in particular along the cylinder 11 or the path of the piston 11A with ongoing dispensing of the injection solution 3. In this way, various positions of the piston 11A can be detected or monitored with various light gates 16.

In particular, multiple light gates 16 with corresponding optical paths 17 are provided distributed at various positions of the cylinder 11 along its cylindrical axis 24 in order to detect various positions of the piston 11A or various fill levels of the injection solution 3.

In this case, as also in comparable cases, the signal 7 can also have multiple partial signals. A number of lines 14 can be provided corresponding to the number of light gates 16 that in each case route a partial signal.

Alternatively, or additionally, multiple light gates 16 or partial signals of the signal 7 that correspond thereto can be brought together. In this case, the signal 7 can have partial signals of the various light gates 16 that can be differentiated, in particular based on varying light intensity and/or based on various wavelengths of the respective light gates

16. In this case, multiple parts of the signal 7 that correspond to partial sensors—in particular in each case to a light gate 16—can optionally be routed over the same line 14.

For example, it can be provided that the light gates 16 have various color filters or operate or are fed with light of various colors. In this case, a common light-supplying line 14 and/or a common line 14 that routes the signal 7 can be sufficient.

In addition, it can be provided that sensors 6 of various measuring principles can be combined with one another, in particular in order to improve reliability. For example, at least one electric sensor 6, which can detect, for example, a change in capacity, a change in inductivity, or the like, can be combined with at least one optical sensor 6, in particular with one or more light gates 16, which detects/detect, for example, in addition the start of injection and/or the end of injection or the start of the movement of the piston 11A or the reaching of an end position with the piston 11A.

Alternatively, or additionally, an acoustic sensor 6 can be provided, in particular a sound sensor 18, such as a microphone, vibration sensor, solid borne sound sensor, or the like. With the sound sensor 18, a signal 7 can be generated, which signal picks up oscillations in particular of the cylinder 11-generated by movement of the piston 11A or dispensing of the injection solution 3 and converts into the signal 7, which accordingly represents these oscillations.

With reference to FIG. 1, it was already mentioned above that the single-use part 2 preferably has the window 4, through which an optical detection of the injection solution 3 and/or of the piston 11A is enabled (in particular by a user), and namely especially preferably along a visual axis 23.

It is preferred that the sensor 6 is provided outside of the window 4 or the visual axis 23. In this way, the sensor 6 does not prevent the view through the window 4 to the injection solution 3 or the piston 11A.

A sensor axis 25 runs preferably crosswise, in particular perpendicular, to the visual axis 23 and preferably to a cylindrical axis 24 of the cylinder 11. In this way, the signal 7 can be generated without the sensor 6 impairing the function of the window(s) 4.

In this regard, preferably an axis that runs in the center through the window 4 and is perpendicular to the cylindrical axis 24 of the cylinder 11 is defined as a visual axis 23. In the case of two opposite windows 4, the visual axis 23 preferably extends in the center through both windows 4. A cylindrical axis 24 is preferably defined as the axis of symmetry of the cylinder 11 or the axis along which the piston 11A can move in the cylinder 11.

The sensor 6 can be provided or arranged for monitoring the injection solution 3, its fill level, or the position of the piston 11A along the sensor axis 25.

In the case of an optical sensor 6 in the form of one or more light gate(s) 16, the sensor axis 25 preferably corresponds to the optical path(s) 17 monitored by the light gate(s) 16. In the case of a capacitive sensor 6, the sensor axis 25 preferably corresponds to the axis through the midpoint of the electrodes 19 or through the midpoints or centers of gravity of the surfaces of the latter that face the cylinder 11.

Referring to FIG. 2, the reusable part 10 has an evaluation system 26 for receiving and/or evaluating the signal 7.

The evaluation system 26 can support a digital signal processing of the signal 7, for example by a processor, storage device, and/or corresponding routines that are filed in the storage device and can be executed by the processor. In this way, the signal 7 can be evaluated; in particular the state or the change in state can be determined, in particular can be calculated from the signal 7.

The evaluation system 26 can form an oscillating circuit with the sensor 6. The resonance frequency of such an oscillating circuit can be evaluated and used for determining the indicator 8. In this case, the signal 7 is preferably formed by the current and/or the voltage or by a (phase) relationship of the latter with respect to one another, which depend on the state or the change in state. In particular, a capacitive sensor 6 can be supplemented by an inductivity or inductive sensor 6 by a capacitor with respect to the oscillating circuit.

The evaluation system 26 is preferably designed for monitoring the injection process. In particular, the electronics 9 can detect with the evaluation system 26 a continuous injection, a primary usefulness or uselessness for this purpose, trigger-readiness, and/or deficient trigger-readiness of the single-use part 2 and can optionally omit the dispensing device 29.

Alternatively, or additionally, the injection device 1 according to the present invention, preferably the electronics 9, in particular the evaluation system 26, is designed for automatic detection of a beginning of injection and/or an end of injection. This can be done in particular by the evaluation of the signal 7 or the detection of the position of the piston 11A.

Figure 6:
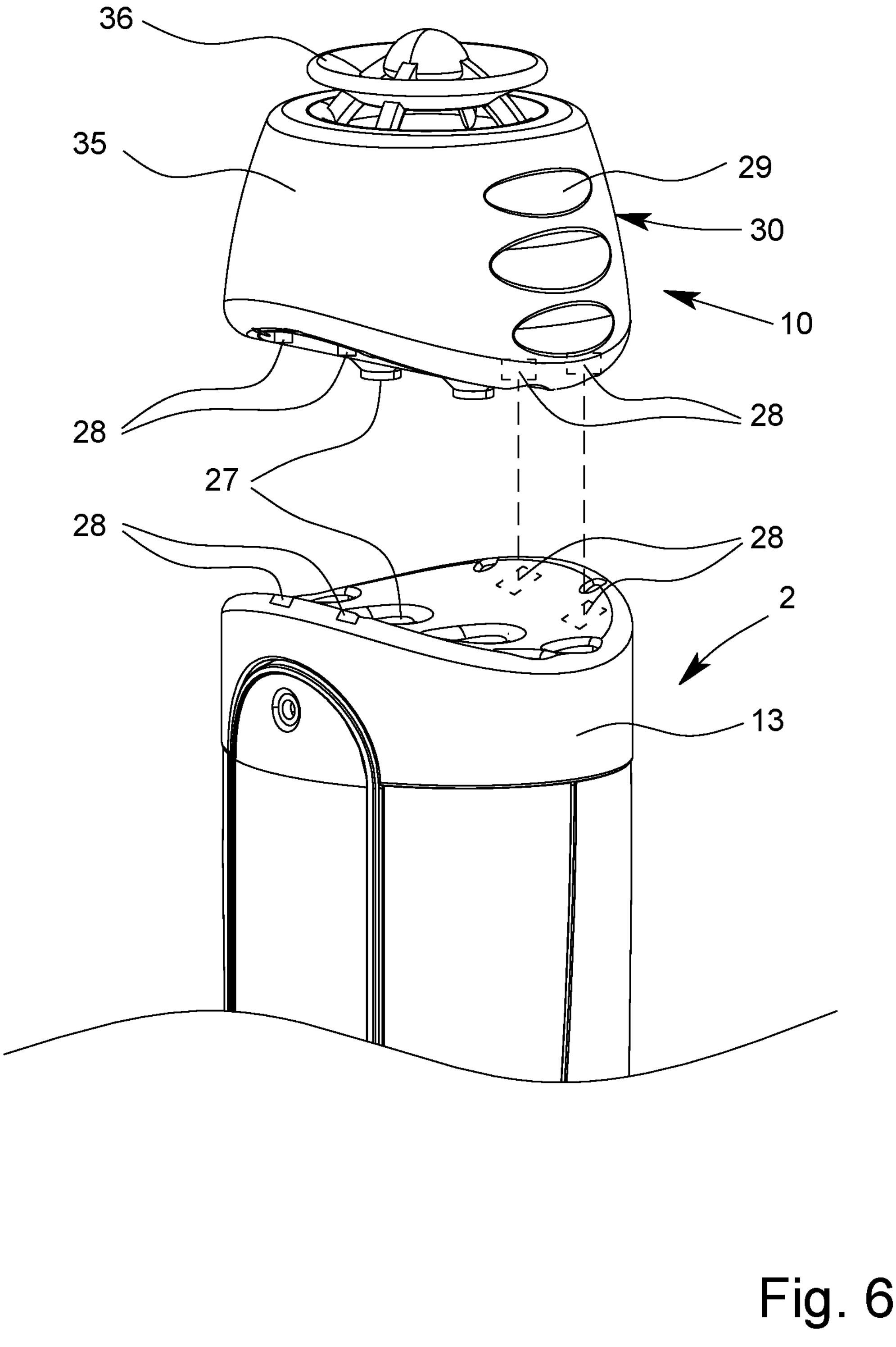
FIG. 6 is a cutaway of an injection device according to the present invention with a reusable part removed from the single-use part.

FIG. 6 shows a cutaway of an injection device 1 according to the present invention with the reusable part 10 removed from the single-use part 2.

For the purpose of evaluation or output, the signal 7 is preferably coupled by the single-use part 2 to the reusable part 10. The single-use part 2 and the reusable part 10 preferably have one or more mutually complementary connectors 27. The connectors 27 are preferably designed to generate the signal connection S during or by the coupling of the single-use part 2 to the reusable part 10. Via the signal connection S, the signal 7 can be transferred between the single-use part 2 and the reusable part 10, or the signal 7 is transferred between the single-use part 2 and the reusable part 10, in particular from the single-use part 2 to the reusable part 10.

Especially preferably, the signal connection S is an optical and/or electrical signal connection S. Accordingly, in the case of the single-use part 2 coupling with the reusable part 10, the connectors 27 can generate the optical and/or electrical signal connection S between the latter, so that an optical or light-based and/or electrical signal 7 can be transferred from the single-use part 2 to the reusable part 10. The connectors 27 can thus be or have or form one or more optical and/or electrical interfaces for light transfer between the single-use part 2 and the reusable part 10.

As already mentioned in connection with FIG. 5, the signal 7 in this illustrative example is preferably an optical signal 7, in particular thus light, which is preferably varied (automatically) as a function of the state or the change in state of the single-use part 2 in the process for dispensing the injection solution 3. In particular, this is done by changes such as movements in the single-use part 2, which can be converted by the sensor 6 into correspondingly changing light intensities of the signal 7.

Accordingly, the signal connection S preferably in this case is an optical signal connection S or the coupling is an optical coupling of the single-use part 2 to the reusable part 10. For this purpose, the connector 27 forms an optical interface or has such a one.

The electronics 9 of the reusable part 10 in this case preferably have a receiver, in particular an electro-optical receiver 31, which is suitable to convert light-based or optical signals 7 into electrical signals 7, which correspond to the light-based or optical signals 7.

Preferably, alternatively or additionally, the reusable part 10 has a preferably optical emitter 32. Via the connectors 27 or the signal connection S, the emitter 32 of the reusable part 10 can supply the sensor 6 of the single-use part 2 preferably with light. In the illustrative example according to FIG. 5 in combination with the schematic representation of FIG. 2, the emitter 32 can be a light source, such as a light-emitting diode (LED).

The emitter 32 can, for example, supply a light gate 16 with light, while the portion of the light that reaches the receiver 31 through the light gate 16 (as optical signal 7) and optionally can be converted into an electrical signal 7, provides information regarding the state or the change in state, in particular with respect to the position of the piston 11A or with respect to the residual volume of available injection solution 3.

The optical signal 7 that is converted into an electrical signal 7 can be analyzed below by the evaluation system 26 in order to determine the state or the change in state of the single-use part 2

The signal 7 or light for forming the signal 7 can be routed starting from the emitter 32 along the housing 13 with or through the housing 13 of the single-use part 2.

The line(s) 14 can bring about a light emission and light inflow to the cylinder 11 that is preferably formed by a glass body or is generally translucent.

In addition, preferably multiple lines 14, in particular at least two lines 14, even more preferably on opposite sides of the cylinder 11, are connected via the optical path 17, which is preferably provided so that the properties of the optical path 17 depend on the state and/or the change in state, so that the (optical) signal 7 can be generated. In this way, one or more light gate(s) 16 can be formed.

The line(s) 14 can be integrated into the housing 13 of the single-use part 2; in particular, they can be formed by light-wave-conducting structures in the housing 13, which are routed from the cylinder 11 to the connectors 27 or via the connectors 27 to the receiver 31 and/or emitter 32.

When multiple sensors 6 are provided, which in each case are designed for generating a signal 7 or a partial signal thereof, the connector 27 can accordingly be designed for coupling multiple (partial) signals 7 from the single-use part 2 to the reusable part 10, and/or the electronics 9, in particular the evaluation system 26, can be designed for evaluating corresponding (partial) signals 7.

If at least one optical sensor 6 as well as a sensor 6 are made based on an electrical operating principle—in particular capacitive or inductive—combined in the single-use part 2, the connector 27 is accordingly preferably designed for generating a signal connection S, which enables both a transfer of optical and electrical signals 7 from the single-use part 2 to the reusable part 10.

Alternatively, or additionally, it is provided that the single-use part 2 and the reusable part 10 have mutually complementary fastening means 28 for reversible mechanical holding of the single-use part 2 and the reusable part 10 together.

In the illustrative example, fastening means 28 are provided both on the single-use part 2 and on the reusable part 10, wherein the fastening means 28 are formed and arranged in a complementary manner to one another in such a way that the reversible holding of the reusable part 10 on the single-use part 2 is enabled.

Quite especially preferably, the fastening means 28 are designed for temporary magnetic holding of the reusable part 10 on the single-use part 2. For this purpose, the single-use part 2 and the reusable part 10 can have magnets or ferromagnetic materials that correspond to one another, which enables the latter to adhere to one another magnetically. In particular, mutually complementary magnets are integrated as fastening means 28 into the single-use part 2 and the reusable part 10. This is indicated in broken lines by way of example in FIG. 6 and depicted schematically in cross-section in FIG. 2.

The fastening means 28 are preferably designed to preset a specific position of the single-use part 2 and the reusable part 10 with respect to one another during coupling of the latter. In particular, the fastening means 28 can specify a position, in particular a rotational position, of the single-use part 2 to the reusable part 10. This position or rotational position is preferably provided in such a way that the signal connection S is reliably produced when the single-use part 2 is coupled to the reusable part 10.

Alternatively, or additionally, the fastening means 28 can prevent coupling or fastening of the reusable part 10 on the single-use part 2 when deviating from the position or rotational position. For example, the fastening means 28 can repel one another, particularly if they are magnetic.

The preset value of the position can be specified by polar-opposite magnets at positions of the single-use part 2 and the reusable part 10 that correspond to one another.

"Rotational position" of the single-use part 2 and the reusable part 10 with respect to one another is preferably a position in which central axes, in particular cylindrical axes of at least essentially cylinder-like or cylindrical housings 13, 35 of the single-use part 2 and the reusable part 10, are arranged coaxially to one another and rotation of the single-use part 2 and the reusable part 10 result in rotational positions of the single-use part 2 to the reusable part 10 that are different with respect to one another. In this context, it is preferably provided that coupling be made possible only at one, two, or specific preset rotational positions with respect to one another and be blocked or prevented at other rotational positions.

Orienting the reusable part 10 to the single-use part 2, in particular a rotational position of the latter with respect to one another, is preferably alternatively or additionally preset by the structural form of the sections or surfaces of the single-use part 2 and the reusable part 10 that are adjacent to one another after coupling has taken place.

In the illustrative example, this is preferably carried out by means of mutually complementary projections and indentations of the single-use part 2 and the reusable part 10 in the area of the connectors 27. In particular, the surfaces to which the reusable part 10 and the single-use part 2 are adjacent after coupling are curved, so that coupling is possible only in one or certain orientations of the reusable part 10 to the single-use part 2.

Alternatively, or additionally, the single-use part 2 has an at least essentially concave shape or surface, while the reusable part 10 has an at least essentially convex shape, reflected thereto, or vice versa, which are adjacent after or by the coupling. In this or another way, a rotation of the reusable part 10 to the single-use part 2—in particular in a positive manner—can be blocked after coupling.

By ensuring that the position or location of the single-use part 2 and the reusable part 10 is a preset value with respect to one another during coupling, a reliable production of the signal connection S can be ensured.

The single-use part 2 can be brought to engagement or engaged specifically with the reusable part 10 in the area of the connector 27; however, the latter otherwise preferably only lie axially behind one another and/or beside one another.

The reusable part 10, in particular the electronics 9, preferably has an output system 29 for generating an output 30, wherein the output 30 is preferably perceptible to a human sense, for example, optically, acoustically, and/or tactilely.

The electronics 9, in particular the output system 29, can have a radio interface, in particular antennae, and, preferably, can be set up for conveying the indicator 8 by radio.

The output system 29 can have a display, one or more LEDs, a loudspeaker, and/or one or more (unbalance) motors, or can be made in this way. A (unbalance) motor is in particular the drive of a vibration alarm for generating a tactile or haptic output 30 that is perceptible to a user.

The output 30 can be the indicator 8, can correspond to the indicator 8, can represent the indicator 8, or can be derived from the indicator 8.

In the illustrative example, an optical output 30 is indicated. For example, the output 30 can represent a status of the injection device 1, in particular that of the single-use part 2, via color coding—such as "green" for trigger-ready or "red" for non-trigger-ready or not to be used—and/or via a position of the output 30. The output 30 is preferably based on the measurement with the sensor 6, evaluation of the signal 7, and/or determination of the indicator 8 on this basis.

In principle, the operation of the window 4 can be replaced by the output 30 by means of the reusable part 10, so that the window 4 can be omitted. The window 4 is preferably provided in addition, however, in order also to enable an optical monitoring of the state or change in state.

As indicated by way of example in FIG. 2, the reusable part 10 can have a reporting system for reporting the presence and/or for identification of a (specific) single-use part 2.

For identification of a specific single-use part 2, the (respective) single-use part 2 can have an identifier 35, such as an RFID transponder, barcode, or the like. In this case, the reporting system 33 can preferably read out the identifier 34 and based on the identifier 34 can determine and optionally output in particular properties of the single-use part 2. The output 30 in this case can be carried out by means of the electronics 9, in particular via the output system 29.

The reusable part 10 preferably has at least essentially completely the electronics 9. In particular, it is preferably provided that the evaluation system 26 as well as possible emitters 32 and/or receivers 31 and/or an energy store 37 exclusively form part of the reusable part 10.

The electronics 9 or the evaluation system 26 has preferably all of the components that are necessary for processing the signal 7. The electronics 9 or evaluation system 26 can be designed for data storage and/or data processing.

The single-use part 2, however, preferably has the sensor 6 that is exclusively required for receiving the signal 7, i.e., in particular no (semiconductor) components, no integrated circuits, no active light sources, no active emitters, and/or no active receivers. The latter can accordingly advantageously be used multiple times because of the preferred integration into the reusable part 10. However, the components that are provided in the single-use part 2, in particular the preferably electrically passive or purely optical sensor 7, in most cases require very little in the way of valuable resources, and the preferably fixed and non-reusable integration of the latter into the single-use part 2 is therefore in practice not disadvantageous.

The electronics 9 can optionally and preferably in addition have one or more other sensors, in particular for a (ambient) temperature, a (relative) humidity, (ambient) light (intensity), or the like. Parameters that are measured herewith can be taken into consideration when the signal 7 is evaluated and/or output with the output system.

In another aspect of this invention, the sensor 6 or the signal 7 is used alternatively or additionally for determining a temperature of the single-use part 2, the cylinder 11, and/or—preferably indirectly—the injection solution 3. In particular, this is an optical sensor 6. The latter can have a dye that, as a function of temperature, changes its absorption properties and/or transmission properties for electromagnetic waves, in particular light. In particular, this is a thermochromic dye. The dye is preferably arranged so that the signal 7 is affected by its absorption properties and/or transmission properties. By acquiring the signal 7, the temperature or a parameter corresponding thereto can be determined accordingly. In particular, the dye is provided in direct contact with the cylinder 11 or as part of it, in particular as part of the cylinder wall 11B or of the material that forms the latter.

Individual aspects of this invention can be implemented in various combinations and can be advantageous in each case based on the combination, even if the latter is not explicitly explained.

The invention claimed is:

1. An injection device, comprising:

a single-use part for dispensing an injection solution having a proximal end face and a distal end face, a multi-use reusable part with electronics having a proximal end face and a distal end face, and a sensor for acquiring a signal with which an indicator representing a state of the single-use part that is associated with the injection process and/or a change in state of the single-use part in a process for dispensing the injection solution with the single-use part, can be determined, wherein the distal end face of the multi-use reusable part with electronics is directly detachably connectable to the proximal end face of the single-use part in a manner enabling a signal to be transferred from the single-use part to the multi-use reusable part when the distal end face of the multi-use reusable part is directly connected to the proximal end face of the single-use part, wherein the proximal end face of the single-use part is at least one of remote from the injection solution or opposite a dispensing outlet of the single-use part;

wherein the sensor is optical and comprises optical wave guides with open ends by which at least one light gate is produced, wherein the optical wave guides are realized by a light-conducting or transparent plastic, which is integrated into the single-use part, wherein the proximal end face of the single-use part and the distal end face of the multi-use reusable part have mutually complementary connectors that connect during coupling to produce the signal connection between the single-use part and the multi-use reusable part for transferring the signal, and wherein the optical wave guides are realized by light-wave-conducting structures in the housing of the single-use part, which are routed in the single-use part to the connectors.

2. The injection device according to claim 1, wherein the optical wave guides are routed along a cylinder of the single-use part.

3. The injection device according to claim 1, wherein the single-use part has a cylinder for taking up the injection solution, a piston that can move in the cylinder for dispensing the injection solution and at least one window, which enables an optical detection of the injection solution and/or of the piston in the cylinder along a visual axis, and wherein the sensor is provided outside of the window and/or the visual axis, at one or more positions on a sensor axis, which runs crosswise to the visual axis and to a cylindrical axis of the cylinder.

4. The injection device according to claim 1, wherein the multi-use reusable part has an evaluation system for determining the indicator by evaluating the signal.

5. The injection device according to claim 1, wherein, only when the single-use part is coupled with the multi-use reusable part is determining the indicator from the signal possible.

6. The injection device according to claim 1, wherein the single-use part and the multi-use reusable part have mutually complementary fastening means for reversible mechanical holding of the single-use part and the multi-use reusable part together.

7. The injection device according to claim 6, wherein the fastening means bring about the mechanical holding magnetically.

8. The injection device according to claim 6, wherein the fastening means being are able to produce temporary magnetic holding of the multi-use reusable part on the single-use part, the single-use part and the multi-use reusable part having magnets or ferromagnetic materials that correspond to one another to adhere one another together magnetically.

9. The injection device according to claim 6, wherein mutually complementary magnets are integrated as fastening means into the single-use part and the multi-use reusable part such that the position of the single-use part and the multi-use reusable part relative to one another is specified by opposite magnets at positions of the single-use part and multi-use the reusable part that correspond to one another.

10. The injection device according to claim 6, wherein the fastening means preset a specific position of the single-use part and the multi-use reusable part with respect to one another during coupling of the latter, wherein, the fastening means specify a position of the single-use part to the multi-use reusable part in such a way that the signal connection is reliably produced when the single-use part is coupled to the multi-use reusable part.

11. The injection device according to claim 1, further comprising an output system for outputting of the indicator.

12. The injection device according to claim 1, wherein the sensor is operable for generating an optical signal that is transferrable exclusively optically to the reusable part, and wherein the multi-use reusable part has an electro-optical receiver for converting the optical signal into an electrical signal corresponding to the optical signal, so that the indicator can be determined by evaluating the electrical signal with the electronics of the multi-use reusable part.

13. The injection device according to claim 1, wherein the multi-use reusable part has a reporting system for detecting the single-use part, the reporting system being able to detect approach of the single-use part and/or to read out an identifier from the single-use part.

14. The injection device according to claim 1, wherein the single-use part has a cylinder for taking up the injection solution and a piston that can move in the cylinder for dispensing the injection solution, wherein at least one light gate is configured to monitor an optical path through the cylinder to enable detecting changes in optical transmission properties as a function of the position of the piston.

15. The injection device according to claim 1, wherein the single-use part has a cylinder for taking up the injection solution and a piston that can move in the cylinder for dispensing the injection solution, wherein multiple light gates are provided at various positions along the cylinder or the path of the piston with ongoing dispensing of the injection solution such that multiple positions of the piston can be detected or monitored with multiple light gates.

16. The injection device according to claim 1, wherein the optical wave guides are made from light-conducting plastic being integrated by means of two-component injection-molding into a housing and/or other component of the single-use part or to be fastened thereby.

17. The injection device according to claim 1, wherein the single-use part has a cylinder for taking up the injection solution and a piston that can move in the cylinder for dispensing the injection solution, and wherein as a function of a fill level of the injection solution in the cylinder or a position of the piston, the optical signal has light or not or is brighter or darker.

18. An injection device, comprising:

a single-use part for dispensing an injection solution having a proximal end face and a distal end face, a multi-use reusable part with electronics having a proximal end face and a distal end face, and an optical sensor for acquiring an optical signal with which an indicator representing a state of the single-use part that is associated with the injection process and/or a change in state of the single-use part in a process for dispensing the injection solution with the single-use part can be determined, wherein the distal end face of the multi-use reusable part is directly detachably connectable to the proximal end face of the single-use part, wherein the single-use part and the multi-use reusable part have mutually complementary connectors that, during direct coupling of the distal end face of the multi-use reusable part to the single-use part, produce an optical signal connection between the single-use part and the multi-use reusable part, the single-use part having a first circumferential wall at the proximal end face and the multi-use reusable part having a second circumferential wall at the distal end face, the first and second circumferential walls aligning with each other when the single-use part and the multi-use reusable part are coupled enabling the optical signal to be transferred from the single-use part to the multi-use reusable part, and wherein the optical sensor comprises optical wave guides that are routed in the single-use part and connected to the connectors, the optical signals being transferable via the optical wave guides from the single-use part to the multi-use reusable part.

19. The injection device according to claim 18, wherein the single-use part and the multi-use reusable part have mutually complementary fastening means for reversible mechanical holding of the single-use part and the multi-use reusable part together.

20. The injection device according to claim 19, wherein mutually complementary magnets are integrated as fastening means into the single-use part and the multi-use reusable part such that the position of the single-use part and the multi-use reusable part relative to one another is specified by opposite magnets at positions of the single-use part and the multi-use reusable part that correspond to one another.

21. The injection device according to claim 19, wherein the fastening means preset a specific position of the single-use part and the multi-use reusable part with respect to one another during coupling of the latter, wherein, the fastening means specify a position of the single-use part to the multi-use reusable part in such a way that the optical signal connection is reliably produced when the single-use part is coupled to the multi-use reusable part.

22. The injection device according to claim 18, wherein the sensor is operable for generating an optical signal that is transferrable exclusively optically to the multi-use reusable part, and wherein the multi-use reusable part has an electro-optical receiver for converting the optical signal into an electrical signal corresponding to the optical signal, so that the indicator can be determined by evaluating the electrical signal with the electronics of the multi-use reusable part.

23. The injection device according to claim 18, wherein the optical wave guides comprise open ends by which at least one light gate is produced.

24. The injection device according to claim 18, wherein the optical wave guides are made from light-conducting plastic being integrated by means of two-component injection-molding into a housing and/or other component of the single-use part or to be fastened thereby.

25. The injection device according to claim 18, wherein the single-use part has a cylinder for taking up the injection solution and a piston that can move in the cylinder for dispensing the injection solution, and wherein as a function of a fill level of the injection solution in the cylinder or a position of the piston, the optical signal has light or not or is brighter or darker.

* * * * *